United States Patent
Koch et al.

(10) Patent No.: US 11,214,555 B2
(45) Date of Patent: Jan. 4, 2022

(54) METHOD FOR DEPLETING 2-METHOXYETHANOL (MOE)

(71) Applicant: BASF SE, Ludwigshafen am Rhein (DE)

(72) Inventors: Eva Koch, Ludwigshafen am Rhein (DE); Oliver Bussmann, Ludwigshafen am Rhein (DE); Joachim Pfeffinger, Ludwigshafen am Rhein (DE); Joerg Pastre, Ludwigshafen am Rhein (DE); Johann-Peter Melder, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/971,660

(22) PCT Filed: Feb. 11, 2019

(86) PCT No.: PCT/EP2019/053269
§ 371 (c)(1),
(2) Date: Aug. 20, 2020

(87) PCT Pub. No.: WO2019/162120
PCT Pub. Date: Aug. 29, 2019

(65) Prior Publication Data
US 2020/0392094 A1 Dec. 17, 2020

(30) Foreign Application Priority Data
Feb. 22, 2018 (EP) .................................. 18158113

(51) Int. Cl.
C07D 295/023 (2006.01)
C07D 295/027 (2006.01)
C07C 41/42 (2006.01)

(52) U.S. Cl.
CPC .......... *C07D 295/027* (2013.01); *C07C 41/42* (2013.01)

(58) Field of Classification Search
CPC .. C07D 295/023; C07D 295/027; C07C 41/42
See application file for complete search history.

(56) References Cited

U.S. PATENT DOCUMENTS

| | | | |
|---|---|---|---|
| 3,154,544 A | 10/1964 | Langdon et al. | |
| 3,155,657 A | 11/1964 | Bedoit, Jr. | |
| 4,256,880 A | 3/1981 | Frech et al. | |
| 4,739,051 A | 4/1988 | Schroeder et al. | |
| 7,825,281 B2 | 11/2010 | Schmidtke et al. | |
| 8,197,646 B2 | 6/2012 | Schmidtke et al. | |
| 8,246,793 B2 | 8/2012 | Schmidtke et al. | |
| 8,293,075 B2 | 10/2012 | Schmidtke et al. | |
| 8,487,135 B2 | 7/2013 | Kubanek et al. | |
| 2008/0255351 A1 | 10/2008 | Hoffer et al. | |

FOREIGN PATENT DOCUMENTS

| | | |
|---|---|---|
| CN | 102002019 A | 4/2011 |
| CN | 102206196 A | 10/2011 |
| CN | 104262173 A | 1/2015 |
| CN | 104262177 A | 1/2015 |
| DE | 1049864 B | 2/1959 |
| DE | 3002342 A1 | 2/1981 |
| DE | 3125662 A1 | 1/1983 |
| DE | 102005047458 A1 | 4/2007 |
| EP | 70397 A1 | 1/1983 |
| EP | 167872 A3 | 12/1986 |
| EP | 514692 A3 | 3/1993 |
| EP | 696572 A1 | 2/1996 |
| WO | WO-2008037587 A1 | 4/2008 |
| WO | WO-2008037589 A1 | 4/2008 |
| WO | WO-2008037590 A1 | 4/2008 |
| WO | WO-2008037659 A1 | 4/2008 |
| WO | WO-2011067199 A1 | 6/2011 |

OTHER PUBLICATIONS

European Search Report for EP Patent Application No. 18158113.3, dated May 23, 2018, 3 pages.
International Preliminary Report on Patentability received for PCT Patent Application No. PCT/EP2019/053269, dated Sep. 3, 2020, 14 pages. (7 pages of English Translation and 7 pages of Original Document).
Roose, et al., "Amines, Aliphatic : 6—Cyclic Amines", Ullmann's Encyclopedia of Industrial Chemistry, Sep. 30, 2015, pp. 21-26.
International Search Report for PCT/EP2019/053269 dated May 2, 2019.
International Search Report for PCT/EP2019/053273 dated Apr. 24, 2019.
Written Opinion of the International Searching Authority for PCT/EP2019/053269 dated May 2, 2019.
Written Opinion of the International Searching Authority for PCT/EP2019/053273 dated Apr. 24, 2019.

*Primary Examiner* — Brenda L Coleman
(74) *Attorney, Agent, or Firm* — Faegre Drinker Biddle & Reath LLP

(57) ABSTRACT

A process for the depletion of 2-methoxyethanol (MOE) from a mixture comprising predominantly morpholine (MO) (crude morpholine), wherein crude morpholine is distilled in a distillation column in the presence of an alkali metal compound of the general formula $M^+[RO^-]$ ($M^+$ is alkali metal cation and R is hydrogen (H), methyl, ethyl, propyl, isopropyl, n-butyl, isobutyl, sec-butyl or tert-butyl), where MO and a compound of the general formula R—OH are distilled off and an alkali metal methoxyethoxide of the general formula $M^+[MeOEtO^-]$ is obtained in the bottom of the column.

16 Claims, No Drawings

METHOD FOR DEPLETING 2-METHOXYETHANOL (MOE)

CROSS-REFERENCE TO RELATED APPLICATIONS

This application is a national stage application (under 35 U.S.C. § 371) of PCT/EP2019/053269, filed Feb. 11, 2019, which claims benefit of European Application No. 18158113.3, filed Feb. 22, 2018, both of which are incorporated herein by reference in their entirety.

The invention relates to a process for the depletion of 2-methoxyethanol from a mixture comprising predominantly morpholine (MO) (crude morpholine).

The separation of 2-methoxyethanol and morpholine is only possible with difficulty on account of the close boiling points. The problem of the depletion of 2-methoxyethanol from a mixture predominantly comprising morpholine arises in particular in connection with the preparation of aminodiglycol (ADG) and morpholine (MO) from the reaction of diethylene glycol (DEG) and ammonia in the presence of hydrogen and a heterogeneous hydrogenation catalyst (catalyst).

Aminodiglycol (ADG) [=2-(2-aminoethoxy)ethanol=2,2'-aminoethoxyethanol] and morpholine are used, inter alia, as solvents, stabilizers, for the synthesis of chelating agents, synthetic resins, medicaments, inhibitors and interface-active substances.

Numerous processes are described in the literature for the preparation of ADG and MO.

Ullmann's Encyclopedia of Industrial Chemistry, 6th Edition, 2000 electronic release, Wiley-VCH Verlag, heading 'Cyclic amines' in the chapter 'Aliphatic amines', describes the synthesis of ADG and MO by amination of DEG under hydrogen pressure and in the presence of a cobalt or nickel catalyst (citations: EP-A-696 572 (BASF AG), DE-A-1 049 864) or other catalysts (citations: DE-A3 002 342, DE-A-3 125 662 (BASF AG), U.S. Pat. No. 3,155,657).

WO 2011/067199 A1 (BASF SE) relates, inter alia, to the reaction of diethylene glycol (DEG) and ammonia in the presence of a supported copper-, nickel- and cobalt-containing catalyst, the catalytically active composition of which prior to reduction thereof with hydrogen ($H_2$) comprises oxygen-containing compounds of aluminum, of copper, of nickel and of cobalt and in the range from 0.2% to 5.0% by weight of oxygen-containing compounds of tin, calculated as SnO.

The three patent applications WO 2008/037587 A1, WO 2008/037589 A1 and WO 2008/037590 A1 (all BASF AG) relate to processes for the continuous distillative separation of mixtures comprising morpholine (MO), monoaminodiglycol (ADG), ammonia and water, obtained by reacting diethylene glycol (DEG) with ammonia.

WO 2008/037659 A1 relates to a process for preparing electronics-grade ADG.

CN 102002019 A describes a distillative method for removing methoxyethanol from morpholine. For this, water vapor is fed into the relevant distillation column. This exploits the fact that methoxyethanol forms an azeotrope with water.

CN 104262173 A and CN 104262177 A both describe a process for reacting DEG with ammonia. CN 104262177 A further describes a process for working up the resulting mixture.

The object of the present invention was to find an improved economical process for the depletion of 2-methoxyethanol from a mixture predominantly comprising morpholine, while overcoming a disadvantage or a plurality of disadvantages of the prior art.

Accordingly, a process has been found for the depletion of 2-methoxyethanol (MOE) from a mixture comprising predominantly morpholine (MO) (crude morpholine), wherein crude morpholine is distilled in a distillation column in the presence of an alkali metal compound of the general formula $M^+[RO^-]$ ($M^+$ is alkali metal cation and R is hydrogen (H), methyl, ethyl, propyl, isopropyl, n-butyl, isobutyl, sec-butyl or tert-butyl), where MO and a compound of the general formula R—OH are distilled off and an alkali metal methoxyethoxide of the general formula $M^+[MeOEtO^-]$ is obtained in the bottom of the column.

The process according to the invention is conducted in a distillation column. All possible distillation columns known to those skilled in the art may be considered. Preference is given to packed columns having structured packings or random packings and also tray columns having trays such as sieve trays, bubble-cap trays or valve trays.

Without restricting the present invention in any way whatsoever, it can be assumed that the 2-methoxyethanol is deprotonated by the hydroxide or alkoxide of the general formula RO and is bound as alkali metal methoxyethoxide in the bottom of the column. A compound of the general formula R—OH, that is to say either water or a corresponding alcohol, is formed from the said hydroxide or alkoxide. These are distilled off. In principle, the use of a plurality of alkali metal compounds is also possible according to the invention.

The process according to the invention can be conducted either continuously or batchwise.

Those skilled in the art will adjust the top pressure and the bottom temperature such that the compound of the general formula R—OH and also morpholine can be distilled off.

Unless explicitly stated otherwise, all specifications of pressure hereinbelow refer to the absolute pressure.

The top pressure in the distillation column is preferably 0.01 to 12 bar, particularly preferably 0.2 to 5 bar and very particularly preferably 0.5 to 3 bar or even 0.5 to 2 bar.

Those skilled in the art will accordingly select the bottom temperature so that for a given top pressure R—OH or morpholine evaporate. For the abovementioned regions for the top pressure, the bottom temperature is typically in the range from 50 to 300° C., particularly preferably 80 to 250° C., very particularly preferably 100 to 200° C.

The top temperature then essentially corresponds to the boiling point of R—OH or morpholine at the respective top pressure set.

It is assumed that under the given distillation conditions the compound R—OH has a lower boiling point than the morpholine. For a batchwise mode of operation, firstly R—OH would therefore be distilled off (the top temperature essentially corresponds to the boiling point of R—OH at the top pressure set) and then morpholine (the top temperature then rises to a value which essentially corresponds to the boiling point of morpholine at the top pressure set).

For a continuous mode of operation it is preferable for crude morpholine and the alkali metal compound to be supplied to the distillation column, for R—OH and optionally R'—OH (as defined hereinbelow) to be removed overhead and for morpholine (MO) to be removed via a side draw, and for alkali metal methoxyethoxide to be discharged via the bottom. In this case, the feed for the alkali metal compound and the side draw at which MO is removed are particularly preferably located in the stripping section of the distillation column. In this case, the feed for the alkali metal compound is very particularly preferably located above the side draw at which morpholine (MO) is removed. Said feed and the side draw are in this case typically located on opposite sides of the distillation column. Especially preferably, the position of the feed for the alkali metal compound in the stripping section of the column is selected such that at that point there is no longer any significant amount of water present. This is to be understood to mean in particular that the water content there is ≤0.1% by weight, in particular ≤0.05% by weight or ≤0.04% by weight, for example 0.01% to 0.03% by weight. The water content can be determined in accordance with DIN EN 51777 (K. Fischer).

In principle, preference can be given to a continuous reaction regime, because this makes it possible to prepare larger quantities of pure, that is to say distilled, morpholine (MO).

The crude morpholine used is typically prepared by reaction of diethylene glycol (DEG) with ammonia and subsequent distillative removal of ammonia, water, aminodiglycol (ADG) and DEG from the reaction product. Such a reaction and removal are described, for example, in WO 2008/037587 A1, WO 2008/037589 A1 and WO 2008/037590 A1 (all BASF AG).

The reaction of DEG and ammonia is typically effected in the presence of hydrogen and a heterogeneous hydrogenation catalyst (catalyst).

In a preferred embodiment (A), a catalyst comprising Cu, Ni, and Co on aluminum oxide as support is used here. Catalysts of this type are described, for example, in WO 2011/067199 A1 (BASF SE).

In a particularly preferred catalyst, the catalytically active composition of the catalyst prior to treatment with hydrogen comprises oxygen-containing compounds of aluminum, of copper, of nickel and of cobalt and in the range from 0.2% to 5.0% by weight of oxygen-containing compounds of tin, calculated as SnO.

In particular, catalysts are used, the catalytically active composition of which, prior to the reduction thereof with hydrogen, comprises in the range from
15% to 80% by weight of oxygen-containing compounds of aluminum, calculated as $Al_2O_3$,
1% to 20% by weight of oxygen-containing compounds of copper, calculated as CuO,
5% to 35% by weight of oxygen-containing compounds of nickel, calculated as NiO,
5% to 35% by weight of oxygen-containing compounds of cobalt, calculated as CoO, and
0.2% to 5.0% by weight of oxygen-containing compounds of tin, calculated as SnO.

The reactor temperature preferred for the reaction of diethylene glycol (DEG) with ammonia is in the range from 170 to 220° C. An isothermal reactor operation mode is preferred. The pressure preferred for the reaction of diethylene glycol (DEG) with ammonia is in the range from 100 to 300 bar.

The reaction of diethylene glycol (DEG) with ammonia is preferably conducted in the presence of hydrogen. The hydrogen is preferably recycled into the reactor as cycle gas via a high-pressure separator.

The molar ratio of ammonia to DEG is preferably in the range from 4 to 10.

The DEG conversion is preferably in the range from 40% to 90%, preferably 50% to 80%, particularly preferably 50% to 75%, or even 50% to 70%.

The catalyst hourly space velocity is generally in the range from 0.05 to 5, preferably 0.1 to 2 kg, of diethylene glycol (DEG) per liter of catalyst (bed volume) and per hour.

The mixture used in the process according to the invention is particularly preferably prepared according to WO 2011/067199 A1 (BASF SE).

In another preferred embodiment, embodiment (B), catalyst, comprising Cu and Ni on aluminum oxide as support, as described in particular in EP-A-70 397 (BASF AG), is used. Catalysts of this type are also described in EP-A-514 692 and EP-A-167 872 (both BASF AG).

In a catalyst which is particularly preferred here, the catalytically active composition of the catalyst prior to treatment with hydrogen comprises in the range from 25% to 65% by weight of aluminum oxide ($Al_2O_3$), 30% to 60% by weight of oxygen-containing compounds of copper, calculated as CuO, and 5% to 15% by weight of oxygen-containing compounds of nickel, calculated as NiO.

The reactor temperature preferred for the reaction of diethylene glycol (DEG) with ammonia is in the range from 190-235° C. here. An isothermal reactor operation mode is preferred. The pressure preferred for the reaction of diethylene glycol (DEG) with ammonia is in the range from 20 to 30 bar.

The molar ratio of ammonia to DEG is preferably in the range from 1:1 to 50:1.

The DEG conversion is preferably in the range from 80% to 98%.

The catalyst hourly space velocity is generally in the range from 0.01 to 2, preferably 0.05 to 0.5 kg, of diethylene glycol (DEG) per liter of catalyst (bed volume) and per hour.

The workup of a mixture obtainable by embodiments (A) and (B), in particular the removal of ammonia, water, aminodiglycol (ADG) and DEG from the reaction product, in order to obtain crude morpholine, is described for example in the application WO 2008/037587 A1 (BASF AG) already mentioned hereinabove.

During the reaction of diethylene glycol (DEG) with ammonia, in addition to aminodiglycol (ADG), morpholine (MO) and the (undesirable) by-product 2-methoxyethanol (MOE), further products of value such as for example N-ethylmorpholine (EMO) and 1,2-ethylenediamine (EDA) are formed.

The crude morpholine preferably comprises >50% by weight, preferably >70% by weight, particularly preferably >85% by weight of morpholine (MO). The crude morpholine typically further comprises <10% by weight, preferably <5% by weight and particularly preferably 0.1% to 5% by weight, for example 0.1% to 1.5% by weight, of methoxyethanol (MOE). The water content is preferably ≤1% by weight, particularly preferably 0.001% to 1% by weight.

The crude morpholine preferably comprises >85% by weight of morpholine (MO) and 0.1% to 5% by weight of methoxyethanol (MOE). The crude morpholine particularly preferably comprises >85% by weight of morpholine (MO), 0.1% to 5% by weight of methoxyethanol (MOE) and ≤1% by weight, in particular 0.001% to 1% by weight, of water.

The precise composition of the crude morpholine depends in particular on how it has been prepared and how the reaction product obtained has been purified (by distillation).

The crude morpholine in particular has
a purity of from 85% to 99% by weight, preferably 85% to 97% by weight,
a content of 1,2-ethylenediamine (EDA) of ≤10% by weight, preferably ≤8% by weight,
a content of N-ethylmorpholine (EMO) of from 0.01% to 0.25% by weight, preferably 0.01% to 0.15% by weight,
a content of 2-methoxyethanol (MOE) of from 0.1% to 5% by weight, preferably 0.1% to 4% by weight, a content of water of ≤1% by weight, preferably 0.001% to 1% by weight.

All weight percentage figures relating to the crude morpholine are based on the total mass of the crude morpholine prior to addition of the alkali metal compound.

If the crude morpholine for example still comprises significant amounts of 1,2-ethylenediamine, this can be removed overhead in the process according to the invention.

It has been recognized according to the invention that any amount, however small, of the alkali metal compound leads in principle to a reduction in the methoxyethanol (MOE) in the distilled morpholine (MO). The alkali metal compound is preferably used in a 0.1-fold to 20-fold (for example 0.2-fold to 10-fold or 0.1-fold to 5-fold), particularly preferably 0.5-fold to 5-fold (for example 1-fold to 5-fold or 1.1-fold to 5-fold), particularly preferably 1.3-fold to 3-fold (for example 1.4-fold to 2.5-fold or 1.5-fold to 2-fold), molar amount based, (a) when an alkali metal hydroxide (alkali metal compound in which R is hydrogen (H)) is used, on the MOE (2-methoxyethanol) present in the crude morpholine,
(b) when an alkali metal alkoxide (alkali metal compound in which R is not hydrogen (H)) is used,
   in a batchwise mode of operation, on the MOE (2-methoxyethanol) present in the crude morpholine and optionally water present in the crude morpholine, or
   in a continuous mode of operation, on the MOE (2-methoxyethanol) present in the crude morpholine.

If the alkali metal compound is not an alkali metal alkoxide but instead an alkali metal hydroxide, the molar amount thus relates exclusively to MOE without taking into account any water that may be present in the crude morpholine. Without in any way restricting the subject matter of the invention, this distinction is based on the following consideration. In the case where an alkali metal alkoxide is used, the alkoxide is protonated by any water that may be present. The alkoxide is then no longer capable of deprotonating an MOE molecule. In the case of an alkali metal hydroxide this plays no role, because protonation of OH⁻ by any water that may be present does not bring about any formal reduction in the molar amount of OH⁻.

If an alkali metal alkoxide is used, a distinction can typically be made between a batchwise and a continuous mode of operation. In the case of a batchwise mode of operation, any water present in the crude morpholine should be taken into account for the reasons mentioned above. In the case of a continuous mode of operation, the position of the feed point is preferably chosen precisely so that at that point there is no longer any significant amount of water present (see hereinabove). This possibility ultimately results from the fact that, under the given distillation conditions, water is a low boiler which is removed overhead, that is to say it accumulates in the rectifying section of the distillation column. Therefore, if the crude morpholine used still comprises small amounts of water, the content of water in the stripping section of the column is correspondingly lower than in the crude morpholine.

$M^+$ (alkali metal cation) is preferably $Li^+$, $Na^+$, or $K^+$, particularly preferably $Na^+$ or $K^+$.

R is preferably methyl, ethyl, propyl, isopropyl, n-butyl, isobutyl, sec-butyl or tert-butyl. That is to say, the use of an alkali metal alkoxide (alkali metal compound of the general formula $M^+[RO^-]$ in which R is not hydrogen (H)) is preferred over the use of an alkali metal hydroxide (alkali metal compound of the general formula $M^+[RO^-]$ in which R is hydrogen (H)). R is particularly preferably methyl, ethyl, propyl or isopropyl and very particularly preferably is methyl or ethyl.

The alkali metal compound is preferably selected from the group consisting of lithium hydroxide, sodium hydroxide, potassium hydroxide, lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, lithium n-butoxide, sodium n-butoxide, potassium n-butoxide, lithium isobutoxide, sodium isobutoxide, potassium isobutoxide, lithium sec-butoxide, sodium sec-butoxide, potassium sec-butoxide, lithium tert-butoxide, sodium tert-butoxide, and potassium tert-butoxide.

The alkali metal compound is particularly preferably selected from the group consisting of lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, lithium n-butoxide, sodium n-butoxide, potassium n-butoxide, lithium isobutoxide, sodium isobutoxide, potassium isobutoxide, lithium sec-butoxide, sodium sec-butoxide, potassium sec-butoxide, lithium tert-butoxide, sodium tert-butoxide, and potassium tert-butoxide.

The alkali metal compound is very particularly preferably selected from the group consisting of lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide.

In a preferred embodiment of the process according to the invention, the alkali metal compound is used in the form of a solution in an alcohol of the general formula R'—OH, in which R' is methyl, ethyl, propyl, isopropyl, n-butyl, isobutyl, sec-butyl or tert-butyl, and R'—OH is likewise distilled off. As already stated above for R—OH, R'—OH will also typically have a lower boiling point than the morpholine under the given distillation conditions. The statements above therefore apply analogously to the distilling-off of R'—OH. If R' corresponds to the radical R, one alcohol is distilled off according to the invention. If the radical R' does not correspond to the radical R, two alcohols are distilled off.

R' is preferably methyl, ethyl, propyl or isopropyl and particularly preferably is methyl or ethyl.

For the (preferred) case where an alkali metal alkoxide is used, the radical R' preferably corresponds to the radical R. This conforms to the usual preparation of an alkali metal alkoxide, where the relevant alkali metal (M) is oxidized in the desired alcohol with the liberation of hydrogen to give the alkali metal cation ($M^+$).

The content of the alkali metal compound in the solution is preferably 1% to 50% by weight, particularly preferably 10% to 40% by weight, very particularly preferably 15% to 40% by weight (based on the total mass of the solution). These figures relate to the solution of the alkali metal compound prior to its addition into the bottom.

In a particularly preferred embodiment of the process according to the invention, the alkali metal compound used is sodium methoxide (20% to 40% by weight in methanol) or potassium ethoxide (15% to 35% by weight in ethanol).

The morpholine (MO) prepared (distilled) using the process according to the invention preferably has a purity of >98.5% by weight, preferably 99.0% by weight.

In addition, the content of methoxyethanol (MOE) is preferably <0.1% by weight, especially <0.05% by weight, in particular <0.03% by weight or even <0.01% by weight.

Preferably, the purity is >98.5% by weight and the content of methoxyethanol (MOE) is <0.1% by weight.

The morpholine (MO) thus prepared (distilled) in particular has
- a purity of >98.5% by weight, preferably >99% by weight, particularly preferably >99.3% by weight,
- a content of 2-methoxyethanol (MOE) of <0.3% by weight, especially <0.1% by weight, in particular <0.03% by weight or even <0.01% by weight,
- a content of N-ethylmorpholine (EMO) of ≤0.20% by weight, in particular ≤0.10% by weight, for example 0.01% to 0.08% by weight,
- a content of 1,2-ethylenediamine (1,2-EDA) of ≤0.30% by weight, in particular ≤0.20% by weight, for example 0.05% to 0.15% by weight, and
- a content of water of ≤0.1% by weight, in particular ≤0.05% by weight or ≤0.04% by weight, for example 0.01% to 0.03% by weight.

Furthermore, the morpholine (MO) prepared may comprise an alcohol of the formula R—OH and optionally of the formula R'—OH at a content of typically ≤1% by weight, preferably ≤0.6% by weight, particularly preferably ≤0.5% by weight.

All weight percentage figures relating to the distilled morpholine are based on the total mass of the distillate obtained after the distillation according to the invention, that is to say morpholine including any secondary components such as MOE, EMO, etc.

The content of morpholine, 2-methoxyethanol, N-ethylmorpholine, 1,2-ethylenediamine and alcohol R—OH and R'—OH in the crude morpholine and in the product of value morpholine can be determined by means of GC. The GC conditions are to be selected in accordance with the corresponding information in the examples section of the application. The water content can be determined in accordance with DIN EN 51777 (K. Fischer).

The examples which follow serve to elucidate the invention without restricting it in any way.

EXAMPLES

The APHA color number was determined in accordance with DIN EN 1557.

The water content was determined in accordance with DIN EN 51777 (K. Fischer).

GC conditions: 30 m Db-1, temperature program with 60° C. starting temperature, 4° C./min heating rate, 190° C. final temperature.

Example 1 (Distillation of Morpholine (MO) in the Presence of Sodium Methoxide)

Column type: 1.0 m Sulzer DX packing,
Diameter 42 mm (A=13.85 cm²)
Number of theoretical plates: 25-30

The reactor was initially charged with 1503 g of crude morpholine (comprising 0.048% by weight of water and 0.4% by weight of MOE) and 32 g of 30% sodium methoxide solution (corresponding to a 1.5-fold molar amount based on MOE and water in the crude morpholine) were added thereto with stirring. The resulting mixture is referred to as feedstock. This was heated to boiling at standard pressure (SP=1.013 bar) and the column was refluxed for 60 minutes. Methanol was removed with a reflux ratio (RR) of 10. After reaching a top temperature of 128° C., the column was switched over to the main run. The two fractions were analyzed by means of gas chromatography (GC).

TABLE 1

Distillation results for sodium methoxide

|  | Feedstock | Fraction 1 | Fraction 2 |
|---|---|---|---|
| Mass/g | 1535 | 107 | 1276 |
| Pressure (top) |  | SP | SP |
| Temperature/° C. (bottom) |  | 129 | 129-137 |
| Temperature/° C. (top) |  | 65-128 | 128 |
| Temperature/° C. (cooler) |  | 20 | 20 |
| APHA color number |  | 10 | 11 |
| Water | 0.00 | 0.07 | 0.02 |
| Methanol/GC area % | 1.47 | 19.70 | 0.05 |
| 2-Methoxyethanol/GC area % | 0.39 | 0.00 | 0.00 |
| 1,2-ethylenediamine/GC area % | 0.00 | 0.57 | 0.00 |
| Morpholine/GC area % | 97.51 | 79.71 | 99.96 |
| Morpholine/g | 1497 | 85 | 1275 |

Result:

Using sodium methoxide, the methoxyethanol was able to be bound in the bottoms during the entire distillation. After the methanol removal, morpholine having a high purity and low color number (fraction 2) could be distilled. The distillation yield for fraction 2 was 85%.

Example 2 (Distillation of Morpholine (MO) in the Presence of Potassium Ethoxide)

The same column type as in example 1 was used.

A reactor was initially charged with 1683 g of crude morpholine (comprising 0.023% by weight of water and 0.4% by weight of MOE) and 58 g of a 24% potassium ethoxide solution (corresponding to a 1.5-fold molar amount based on MOE and water in the crude morpholine) were added thereto with stirring. The resulting mixture is referred to as feedstock. This was then heated to boiling at standard pressure (SP) and the column was refluxed for 60 minutes. Ethanol was removed with a reflux ratio (RR) of 10 to 15. After reaching a top temperature of 128° C., the column was to the main run. The fractions were analyzed by means of GC.

TABLE 2

Distillation results for potassium ethoxide

|  | Feedstock | Fraction 1 | Fraction 2 | Fraction 3 |
|---|---|---|---|---|
| Mass/g | 1741 | 268 | 160 | 1193 |
| Pressure (top) |  | SP | SP | SP |
| Temperature/° C. (bottom) |  | 128-129 | 129 | 129 |
| Temperature/° C. (top) |  | 77-127 | 127-128 | 128 |
| Temperature/° C. (cooler) |  | 20 | 20 | 20 |
| APHA color number |  |  |  | 11 |
| Water | 0.00 |  |  | 0.016 |
| Ethanol/GC area % | 2.53 | 17.72 | 0.77 | 0.10 |
| 2-Methoxyethanol/GC area % | 0.39 | 0.00 | 0.00 | 0.00 |

TABLE 2-continued

Distillation results for potassium ethoxide

|  | Feedstock | Fraction 1 | Fraction 2 | Fraction 3 |
|---|---|---|---|---|
| 1,2-ethylenediamine/GC area % | 0.00 | 0.00 | 0.00 | 0.00 |
| Morpholine/GC area % | 96.29 | 80.44 | 98.93 | 99.85 |
| Unknown/GC area % | 0.00 | 0.04 | 0.27 | 0.04 |
| Morpholine/g | 1677 | 216 | 158 | 1191 |

Result:

Using potassium ethoxide, the methoxyethanol was able to be bound in the bottoms during the entire distillation. After the ethanol removal, morpholine having a high purity and low color number could be distilled. The distillation yield for fraction 3 was 71%.

Example 3 (Distillation of Morpholine (MO) in the Presence of Sodium Hydroxide)

The same column type as in example 1 was used.

A reactor was initially charged with 1682 g of crude morpholine (comprising 0.4% by weight of MOE and 0.00% by weight of water) and 28.4 g of a 23.3% methanolic NaOH solution (corresponding to a 1.86-fold molar amount based on MOE in the crude morpholine) were added thereto with stirring. The mixture was then heated to boiling at SP and the column was refluxed for 60 minutes. Methanol was removed with an RR of 15. From a top temperature of 128° C., the column was switched over to the main run. The top cooler was operated at a temperature of 75° C. (partial condenser).

TABLE 3

Distillation results for sodium hydroxide

|  | Feedstock | Fraction 1 | Fraction 2 | Fraction 3 |
|---|---|---|---|---|
| Mass/g | 1710 | 185 | 147 | 1261 |
| Pressure (top) |  | SP | SP | SP |
| Temperature/° C. (bottom) |  | 130 | 129 | 129-145 |
| Temperature/° C. (top) |  | 114-128 | 128 | 128 |
| Temperature/° C. (cooler) |  | 75 | 75 | 75 |
| APHA color number |  |  |  | 0.04 |
| Water | 0.00 |  |  | 0.016 |
| Methanol/GC area % | 1.27 | 13.33 | 0.51 | 0.10 |
| 2-Methoxyethanol/GC area % | 0.39 | 0.00 | 0.00 | 0.03 |
| 1,2-ethylenediamine/GC area % | 0.00 | 0.00 | 0.00 | 0.00 |
| Morpholine/GC area % | 97.95 | 86.47 | 99.38 | 99.83 |
| Unknown/GC area % | 0.00 | 0.11 | 0.12 | 0.00 |
| Morpholine/g | 1675 | 160 | 146 | 1259 |

Result:

Using NaOH, the methoxyethanol was for the most part able to be bound in the bottoms during the entire distillation. After the methanol removal (fractions 1 and 2), morpholine having a high purity and low color number (fraction 3) could be distilled. The distillation yield for fraction 3 was 75%.

Example 4 (Continuous or Semi-Batchwise Distillation of Morpholine (MO) in the Presence of Sodium Methoxide)

Column type: 1.5 m Sulzer DX packing,
Diameter 30 mm
Number of theoretical plates: 30-45
Continuous Mode of Operation (Fraction 1):

The reactor was initially charged with 500 g of crude morpholine (comprising 0.02% by weight of water and 0.26% by weight of MOE) and 4.8 g of 30% sodium methoxide solution were added thereto with stirring. The resulting mixture was then heated to boiling at SP and the column was refluxed for 30 minutes. Morpholine was distilled with an RR of 3. At the same time, MOE-containing morpholine and sodium methoxide were metered into the bottom of the distillation. In order to selectively remove methanol, the top cooler was operated as a partial condenser at approx. 80° C. Fraction 1 was condensed, with the predominant portion of the methanol remaining in the gas phase. The methanol was then condensed in a second, downstream condenser. After 26 h, the experiment was stopped. The results show a marked depletion of methoxyethanol in fraction 1.

Semi-Batchwise Mode of Operation (Fractions 2 and 3):

The reactor was initially charged with 730 g of crude morpholine (comprising 0.02% by weight of water and 0.26% by weight of MOE) and 48.5 g of 30% sodium methoxide solution were added thereto with stirring. The resulting mixture was then heated to boiling at SP and the column was refluxed for 30 minutes. Morpholine was distilled with an RR of 3. At the same time, MOE-containing morpholine was metered into the bottom of the distillation. The methanol was removed in exactly the same way as in the continuous mode of operation. The results show a marked depletion of methoxyethanol in fraction 2.

After 8 h, the feed amount of morpholine was increased from 300 to 400 g/h and the purified morpholine was collected as fraction 3. After 9 h, the experiment was ended. An increased content of methoxyethanol can be observed in fraction 3 compared to fractions 1 and 2. This is associated with the fact that no further new sodium methoxide was added, that is to say the sodium methoxide was no longer available in an amount sufficient to quantitatively bind the methoxyethanol in the bottoms. This proves that the binding of the methoxyethanol in the bottoms can be attributed to the presence of the sodium methoxide.

|  | Feedstock | Fraction 1 | Fraction 2 | Fraction 3 |
|---|---|---|---|---|
| Mass/g | 12 805 g of crude MO and 128 g of Na methoxide | 185 | 147 | 1261 |
| Pressure (top) |  | SP | SP | SP |
| Temperature/° C. (bottom) |  | 129-130 | 129-130 | 130 |
| Temperature/° C. (top) |  | 126 | 126 | 126-127 |
| Temperature/° C. Partial condenser |  | 75-80 | 80 | 80 |
| Temperature/° C. (cooler) |  | 20 | 20 | 20 |
| APHA color number | 5 | 10 | 11 | 10 |
| Water | 0.020 | 0.065 | 0.006 | 0.002 |
| Methanol/GC area % | 0.560 | 0.492 | 0.099 | 0.027 |

-continued

|  | Feedstock | Fraction 1 | Fraction 2 | Fraction 3 |
|---|---|---|---|---|
| 2-Methoxyethanol/GC area % | 0.261 | 0.008 | 0.003 | 0.023 |
| 1,2-ethylenediamine/GC area % | 0.00 | 0.036 | 0.018 | 0.011 |
| Morpholine/GC area % | 98.939 | 99.453 | 99.870 | 99.932 |
| Morpholine/g | 12 669 | 5444 | 2534 | 2884 |

The values given in the "Feedstocks" column relate to the feed stream into the column The distillation yield for the fractions 1 to 3 was 86%.

The invention claimed is:

1. A process for the depletion of 2-methoxyethanol (MOE) from a mixture comprising predominantly morpholine (MO) (crude morpholine), wherein crude morpholine is distilled in a distillation column in the presence of an alkali metal compound of the formula $M^+[RO^-]$ ($M^+$ is alkali metal cation and R is hydrogen (H), methyl, ethyl, propyl, isopropyl, n-butyl, isobutyl, sec-butyl or tert-butyl), where MO and a compound of the formula R—OH are distilled off and an alkali metal methoxyethoxide of the formula $M^+[MeO-EtO^-]$ is obtained in the bottom of the column.

2. The process according to claim 1, wherein the alkali metal compound is used in a 0.1-fold to 5-fold molar amount based,
   (a) when an alkali metal hydroxide (alkali metal compound in which R is hydrogen (H)) is used, on the MOE (2-methoxyethanol) present in the crude morpholine,
   (b) when an alkali metal alkoxide (alkali metal compound in which R is not hydrogen (H)) is used,
      in a batchwise mode of operation, on the MOE (2-methoxyethanol) present in the crude morpholine and optionally water present in the crude morpholine, or
      in a continuous mode of operation, on the MOE (2-methoxyethanol) present in the crude morpholine.

3. The process according to claim 1, wherein $M^+$ is $Li^+$, $Na^+$ or $K^+$.

4. The process according to claim 1, wherein the alkali metal compound is selected from the group consisting of lithium hydroxide, sodium hydroxide, potassium hydroxide, lithium methoxide, sodium methoxide, potassium methoxide, lithium ethoxide, sodium ethoxide, potassium ethoxide, lithium propoxide, sodium propoxide, potassium propoxide, lithium isopropoxide, sodium isopropoxide, potassium isopropoxide, lithium n-butoxide, sodium n-butoxide, potassium n-butoxide, lithium isobutoxide, sodium isobutoxide, potassium isobutoxide, lithium sec-butoxide, sodium sec-butoxide, potassium sec-butoxide, lithium tert-butoxide, sodium tert-butoxide, and potassium tert-butoxide.

5. The process according to claim 1, wherein the alkali metal compound is used in the form of a solution in an alcohol of the formula R'—OH, in which R' is methyl, ethyl, propyl, isopropyl, n-butyl, isobutyl, sec-butyl or tert-butyl, and R'—OH is likewise distilled off.

6. The process according to claim 5, wherein in the case where an alkali metal alkoxide is used, the radical R' corresponds to the radical R.

7. The process according to claim 5, wherein the content of the alkali metal compound in the solution is 1% to 50% by weight (based on the total mass of the solution).

8. The process according to claim 5, wherein the alkali metal compound used is sodium methoxide (20% to 40% by weight in methanol) or potassium ethoxide (15% to 35% by weight in ethanol).

9. The process according to claim 1, wherein the crude morpholine is obtained by reaction of diethylene glycol (DEG) with ammonia and subsequent distillative removal of ammonia, water, aminodiglycol (ADG) and DEG from the reaction product.

10. The process according to claim 1, wherein the crude morpholine comprises >85% by weight of morpholine (MO) and 0.1% to 5% by weight of methoxyethanol (MOE).

11. The process according to claim 1, wherein the morpholine (MO) distilled off has a purity of >98.5% by weight and a content of methoxyethanol (MOE) of <0.1% by weight.

12. The process according to claim 1, wherein the top pressure in the distillation column is 0.01 to 12 bar.

13. The process according to claim 1, wherein for a continuous mode of operation crude morpholine and the alkali metal compound are supplied to the distillation column, R—OH is removed overhead and MO is removed via a side draw, and alkali metal methoxyethoxide is discharged via the bottom.

14. The process according to claim 13, wherein the feed for the alkali metal compound and the side draw at which MO is removed are located in the stripping section of the distillation column.

15. The process according to claim 14, wherein the feed for the alkali metal compound is located above the side draw at which MO is removed.

16. The process according to claim 15, wherein the position of the feed for the alkali metal compound in the stripping section of the column is selected such that there is no significant amount of water present there.

* * * * *